United States Patent [19]

Brawer

[11] Patent Number: 5,688,694
[45] Date of Patent: Nov. 18, 1997

[54] METHOD FOR ESTIMATING THE BIOLOGIC POTENTIAL OF A SELECTED CARCINOMA IN A PATIENT

[75] Inventor: Michael K. Brawer, Mercer Island, Wash.

[73] Assignee: University of Washington, Seattle, Wash.

[21] Appl. No.: 351,724

[22] Filed: Dec. 7, 1994

Related U.S. Application Data

[63] Continuation of Ser. No. 821,120, Jan. 15, 1992, abandoned.
[51] Int. Cl.⁶ .................... G01N 33/574; G01N 33/483
[52] U.S. Cl. .................... 436/64; 435/7.23; 436/63; 436/813
[58] Field of Search .................... 128/749, 4; 435/7.23, 435/960; 436/63, 64, 813

[56] References Cited

PUBLICATIONS

H.C. Van Der Linden et al., "Morphometry and Breast Cancer: II. Characterization of Breast Cancer Cells with High Malignant Potential in Patients with Spread to Lymph Nodes", *Biological Abstracts* 82:1986, Abstract No. 64957.

Shingo Takano et al., "Ultrastructure of Glioma Vessel: Morphometric Study for Proliferative Potential of Endothelial Cells" *Biological Abstracts* 92: 1991, Abstract No. 30882.

Weidner et al., "Tumor Angiogenesis and Metastasis—Correlation in Invasive Breast Carcinoma," *New Eng. J. Med.* 324(1):1–8, 1991.

Brem et al., "Tumor Angiogenesis: A Quantitative Method for Histologic Grading," *J. Natl. Cancer Inst.* 48(2):347–356, 1972.

Sillman et al., "The Significance of Atypical Vessels and Neovascularization in Cervical Neoplasia," *Am. J. Obstet. Gynecol.* 139(2):154–159, 1981.

Zincke et al., "Relationship Between Grade and Stage of Adenocarcinoma of the Prostate and Regional Pelvic Lymph Node Metastases," *J. Urology* 128:498–501, 1982.

Srivastava et al., "The Prognostic Significance of Tumor Vascularity in Intermediate–Thickness (0.76–4.0 mm Thick) Skin Melanoma," *Am. J. Path.* 133(2):419–423, 1988.

Srivastava et al., "Neovascularization in Human Cutaneous Melanoma: A Quantitative Morphological and Doppler Ultrasound Study," *Eur. J. Cancer Clin. Oncol.* 22(10):1205–1209, 1986.

Yamaura and Sato, "Quantitative Studies on the Developing Vascular System of Rat Hepatoma," *J. Natl. Cancer Inst.* 53(5):1229–1240, 1974.

Chodak et al., "Angiogenic Activity as a Marker of Neoplastic Lesions of the Human Bladder," *Ann Surg.* 192(6):762–771, 1980.

Folkman, "What Is the Evidence That Tumors Are Angiogenesis Dependent," *J. Natl. Cancer Inst.* 82(1):4–6, 1990.

Jensen et al., "Angiogenesis Induced by Normal Human Breast Tissue: A Probable Marker for Precancer," *Science* 218:293–295, 1982.

Liotta et al., "Quantitative Relationships of Intravascular Tumor Cells, Tumor Vessels, and Pulmonary Metastases Following Tumor Implantation," *Cancer Research* 34:997–1004, 1974.

Paulson et al., "Predictors of Lymphatic Spread in Prostatic Adenocarcinoma: Uro–Oncology Research Group Study,"0 *J. Urology* 123:697–699, 1980.

Khominsky and Schamaev, "Über die Vaskularisation der neuroektodermalen Geschwülste von Verschiedenen Malignitätsgraden," *Arch. Geschwulsforsch.* 37(2):136–151, 1971 (describes vascularization of neuroectodermal tumors of various malignancy grades).

Tropé, "The Preoperative Diagnosis of Malignancy of Ovarian Cysts," *Neoplasma* 28(1):117–121, 1981.

McCullough et al., "Carcinoma of the Prostate and Lymphatic Metastases," *J. Urology* 111:65–71, 1974.

Maiorana and Gullino, "Acquisition of Angiogenic Capacity and Neoplastic Transformation in the Rat Mammary Gland," *Cancer Research* 38:4409–4414, 1978.

Folkman and Klagsbrun, "Angiogenic Factors," *Science* 235:442–447, 1987.

Folkman et al., "Induction of Angiogenesis During the Transition from Hyperplasia to Neoplasia," *Nature* 339:58–61, 1989.

Brem et al., "Angiogenesis as a Marker of Preneoplastic Lesions of the Human Breast," *Cancer* 41:239–244, 1978.

Brem et al., "Angiogenesis: A Marker for Neoplastic Transformation of Mammary Papillary Hyperplasia," *Science* 195:880–882, 1977.

Chandrasekhar et al., "Ultrasonically Guided Percutaneous Biopsy of Peripheral Pulmonary Masses," *Chest* 70(5):627–630, 1976.

Sawhney et al., "Tru–Cut Biopsy of Mediastinal Masses Guided by Real–Time Sonography," *Clinical Radiology* 44:16–19, 1991.

Tatematsu et al., "Neovascularization in Benign and Malignant Urinary Bladder Epithelial Proliferative Lesions of the Rat Observed *In Situ* by Scanning Electron Microscopy and Autoradiography," *Cancer Research* 38:1792–1800, 1978.

Ackerman, "The Blood Suply of Experimental Liver Metastases. IV. Changes in Vascularity with Increasing Tumor Growth," *Surgery* 75(4):589–596, 1974.

(List continued on next page.)

*Primary Examiner*—Toni R. Scheiner
*Attorney, Agent, or Firm*—Seed and Berry LLP

[57] ABSTRACT

A method for estimating the biologic potential of prostate carcinoma in a patient is disclosed, comprising the steps of (a) obtaining a limited random biopsy sample of prostate carcinoma from a patient, and (b) quantifying the vascularity of the biopsy, and therefrom estimating the metastatic potential of the prostate carcinoma. Also disclosed is a method for estimating the biologic potential of a selected carcinoma in a patient, comprising the steps of (a) obtaining a limited random biopsy specimen from a carcinoma by a method selected from the group consisting of needle biopsy, endoscopy, laproscopy, and cystoscopy, and (b) quantifying the vascularity of the biopsy specimen, and therefrom estimating biologic potential of the selected carcinoma.

3 Claims, 5 Drawing Sheets

PUBLICATIONS

Brem, "The Role of Vascular Proliferation in the Growth of Brain Tumors," *Clinical Neurosurgery*, Ch. 33, pp. 440–453, 1975.

Auerbach, "Angiogenesis Induction by Tumors, Embryonic Tissues, and Lymphocytes," *Cancer Research* 36:3435–3440, 1976.

Kramer et al., "Comparative Morphology of Primary and Secondary Deposits of Prostatic Adenocarcinoma," *Cancer* 48(2):271–273, 1981.

Rastinejad et al., "Regulation of the Activity of a New Inhibitor of Angiogenesis by a Cancer Suppressor Gene," *Cell* 56:345–355, 1989.

Folkman and Cotran, "Relation of Vascular Proliferation to Tumor Growth," pp. 207–248.

Folkman, J., "Tumor Angiogenesis: Therapeutic Implications," *New Eng. J. Med.* 285(21):1182–1186, 1971.

METHOD FOR ESTIMATING THE BIOLOGIC POTENTIAL OF A SELECTED CARCINOMA IN A PATIENT

CROSS-REFERENCE TO RELATED APPLICATION

This application is a continuation of U.S. Ser. No. 07/821,120, filed Jan. 15, 1992, which application has been abandoned.

TECHNICAL FIELD

The present invention relates generally to the analysis of carcinomas, and more particularly, to methods for estimating the biologic potential of carcinomas, especially prostate carcinomas.

BACKGROUND OF THE INVENTION

Successful treatments for most types of cancer are readily available in the form of surgical and chemotherapeutic techniques which dramatically increase survival for patients who receive accurate and timely diagnoses. Unfortunately, even though a physician may be able to predict whether a patient's tumor is "benign" or "malignant," the reliability and significance of this prediction is uncertain. Most commonly, a diagnosis of malignancy depends on histopathological findings, determined by microscopic analysis of biopsies or other tissue samples taken from the patient. Histopathologic diagnosis of cancer presents a number of major drawbacks, not the least important of which are that: i) using currently available techniques, histopathologic assessment of tumor malignancy often requires relatively extensive tissue sampling, so that in many cases low-morbidity sampling techniques such as needle biopsy cannot be applied in a clinically useful manner; ii) histopathologic markers for malignancy are typically assessed qualitatively, leaving a wide margin for error and discrepancy between individual pathologists in evaluating samples; and iii) histopathologic markers for malignancy vary widely between different forms of cancer, making a standard method of analysis impracticable. Because of this situation, individual histopathologists may require special training to expertly diagnose specific forms of cancer, or may be poorly qualified for diagnosing a wide range of cancers. For most forms of cancer, the term malignancy actually embraces a broad spectrum of disease states, or so-called "grades" of malignancy. Different schools of teaching may apply different grading systems to the same form of cancer, while grading systems for different forms of cancer may be entirely incomparable. These circumstances add further uncertainty to the qualitative histopathologic diagnosis of cancer.

Even if methods for predicting tumor malignancy were considerably easier, and less risky and prone to error, cancer diagnostic methods would remain critically flawed since it is still unclear how tumor malignancy relates to the ability of a tumor to metastasize, or spread from its site of origin. Although it is generally accepted that a "benign" tumor poses little or no threat of metastasis, and that tumors of low and high grade malignancy pose lesser or greater threats of metastasis, respectively, a reliable and direct correlation between the biologic potential to metastasize, and malignancy grade is conspicuously absent for all forms of cancer. This suggests that factors other than cellular differentiation are responsible for a tumor cell's ability to metastasize (see Kramer et al., Cancer 48:271–273, 1981). These circumstances also imply that a significant percentage of intermediate grade malignancies actually possess unforeseeably low biologic potentials. Unfortunately, in such a case, the physician might be compelled to employ therapy such as surgery, radiation, or chemotherapy, even though such treatments may in fact decrease the patient's chances for survival or result in significant morbidity. Conversely, life-saving treatments may often be withheld from patients who present lower grade malignancies, which actually possess high potentials for metastasis. To provide more effective tools for cancer diagnosis, it is therefore necessary to develop technologies to determine the biologic potential of carcinomas directly. Such technologies call for discovery of relevant "markers" of biologic potential, and development of tools to evaluate and measure these markers. An optimal technology of this sort should be applicable with minimal risk and morbidity to a wide range of cancers, and be quantitative, reproducible, and require minimal expenditure of time and expertise.

Previous attempts to develop such diagnostic methods for determining the biologic potential of carcinomas began with studies comparing malignancy grade in primary tumors with the presence or absence of lymphatic metastases in patients (see for example, Paulson et al., J. Urology 123:697–699, 1980, and Kramer et al., Cancer 48:271–273, 1981). These efforts suggested only a rough correlation between malignancy grade and metastasis, and biologic potential appeared unrelated to malignancy grade in the most common, intermediate grade tumors. Further, these studies typically involved histopathological analyses of whole organs, or large tissue samples obtained by surgery.

From this discussion, it is evident that there is a need for clinically useful methods for estimating biologic potential of carcinomas in patients. The present invention fulfills this need and provides other related advantages.

SUMMARY OF THE INVENTION

Briefly stated, the present invention provides methods for estimating the biologic potential of selected carcinomas, particularly prostate carcinomas, within a patient. Within one aspect of the present invention, a method for estimating the biologic potential of prostate carcinoma in a patient is provided, comprising the steps of: (a) obtaining a tissue sample of prostate carcinoma from a patient; and (b) quantifying the vascularity of the tissue sample, and therefrom estimating the biologic potential of the prostate carcinoma. Such a tissue sample may be obtained, for example, by needle biopsy, transurethral biopsy or resection, or surgical excision of the prostate. The vascularity of the tissue sample may be quantified by a variety of methods, including for example, manual or computer-aided morphometric quantification.

Within a related aspect of the present invention, a method for estimating the biologic potential of a selected carcinoma in a patient is provided, comprising the steps of: (a) obtaining a biopsy specimen from a carcinoma by a method selected from the group consisting of needle biopsy, endoscopy, laproscopy, and cystoscopy; and (b) quantifying the vascularity of the biopsy specimen, and therefrom estimating the biologic potential of the cancer. Representative examples of such carcinomas include head and neck tumors, CNS tumors, melanomas and other skin tumors, lymphomas, soft tissue sarcomas, and, breast, bladder, pancreatic, colon, urothelial, testicular, cervical, uterine, renal, ovarian, hepatic, pulmonary, esophageal, and gastric carcinomas.

These and other aspects will become evident upon reference to the following description and attached drawings.

DETAILED DESCRIPTION OF THE INVENTION

Figure 1A:
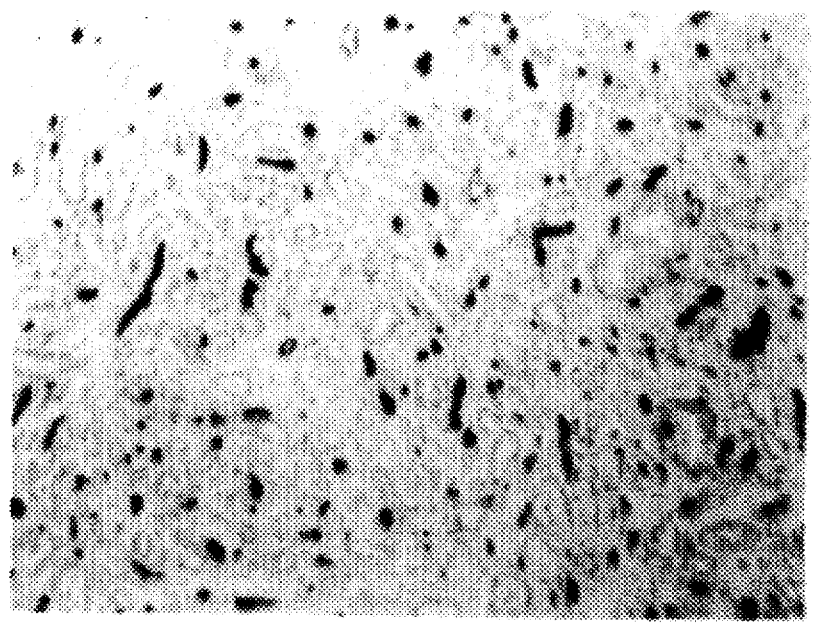
FIGS. 1A and 1B are photographs of Factor VIII stained blood vessels from an area of prostatic carcinoma which has been digitized. In the top photograph (a), unaltered digitized image before analysis is shown. In the bottom photograph (b), the same image after operator manipulation and application of OPTIMAS image analysis software is shown (100×).
Figure 1B:
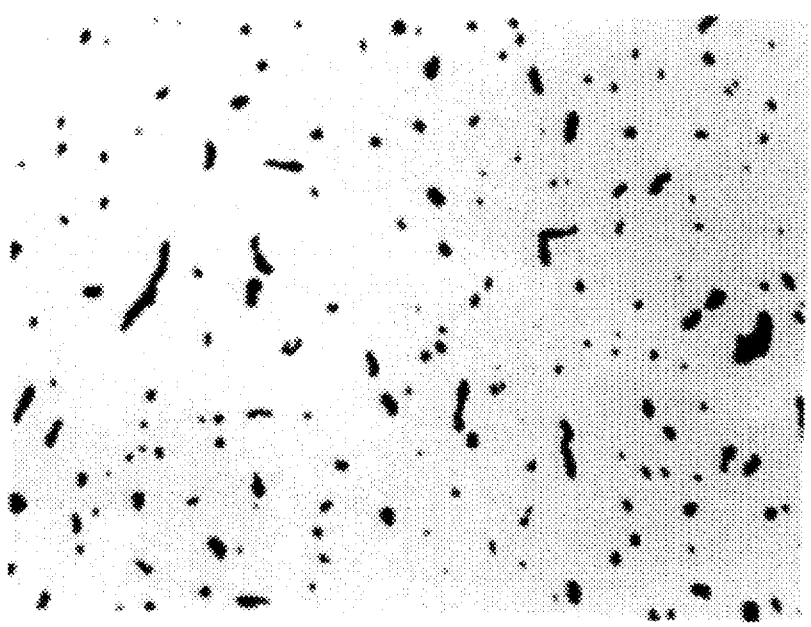
Figure 2A:
FIGS. 2A and 2B are photographs of benign prostatic glandular tissue. In the top photograph (a) a hematoxylin and eosin (H and E) stained section is shown. In the bottom photograph (b) a serial section stained with antibody to Factor VIII is shown. There is normal distribution of capillaries adjacent to glands with a few larger vessels within the intervening stroma (115×).
Figure 2B:
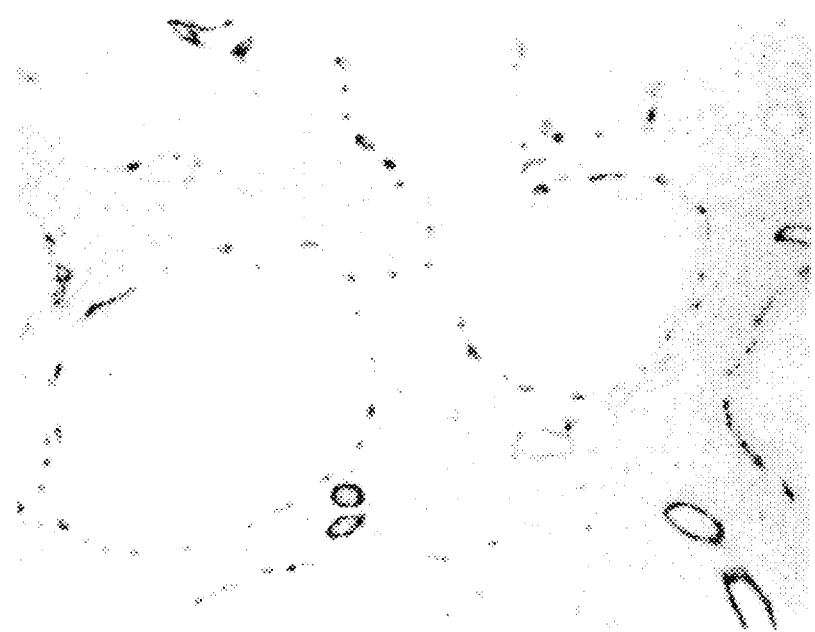
Figure 3A:
FIGS. 3A and 3B are photographs of benign prostatic glands stained with antibody to Factor VIII. The top photograph (a) depicts a portion of a gland containing normal columnar epithelium with a high density of capillaries adjacent to the basal epithelial cells. There is an absence of vessels in the surrounding stroma. The bottom photograph (b) shows a portion of a dilated gland with atrophic low cuboidal epithelium, with low density of adjacent capillaries (312×).
Figure 3B:
Figure 4A:
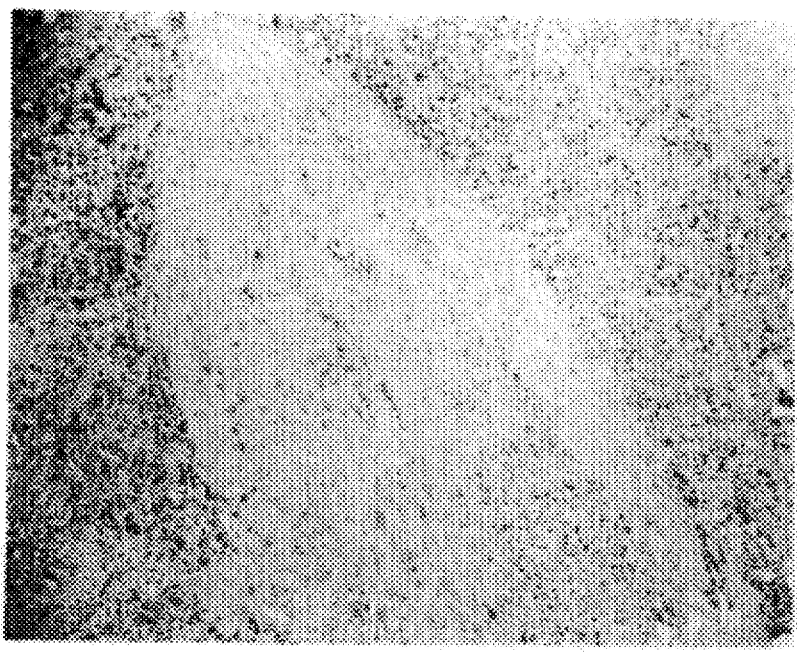
FIGS. 4A and 4B are photographs of infiltrating high grade carcinoma invading prostatic stroma. The top photograph (a) shows an H and E stained section. The bottom photograph (b) is of the same area stained with Factor VIII antibody, demonstrating numerous capillaries in the carcinoma (100×).
Figure 4B:
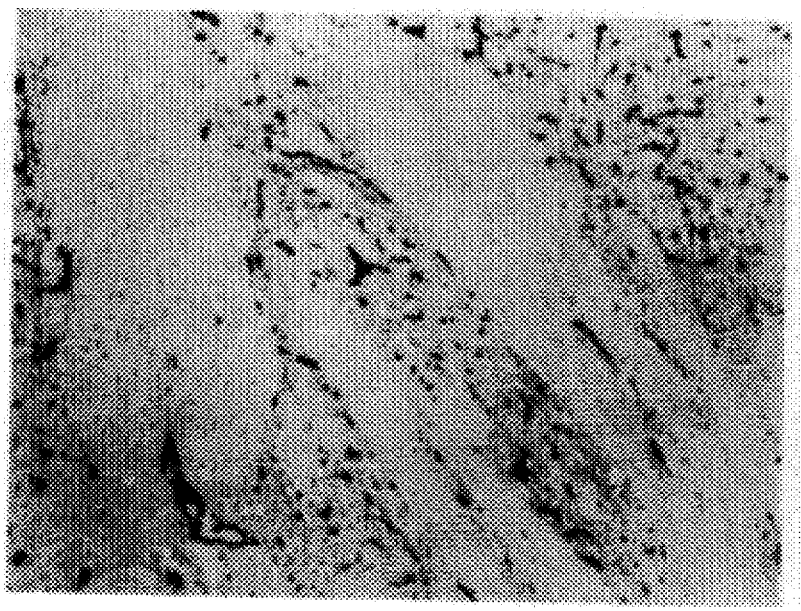
Figure 5:
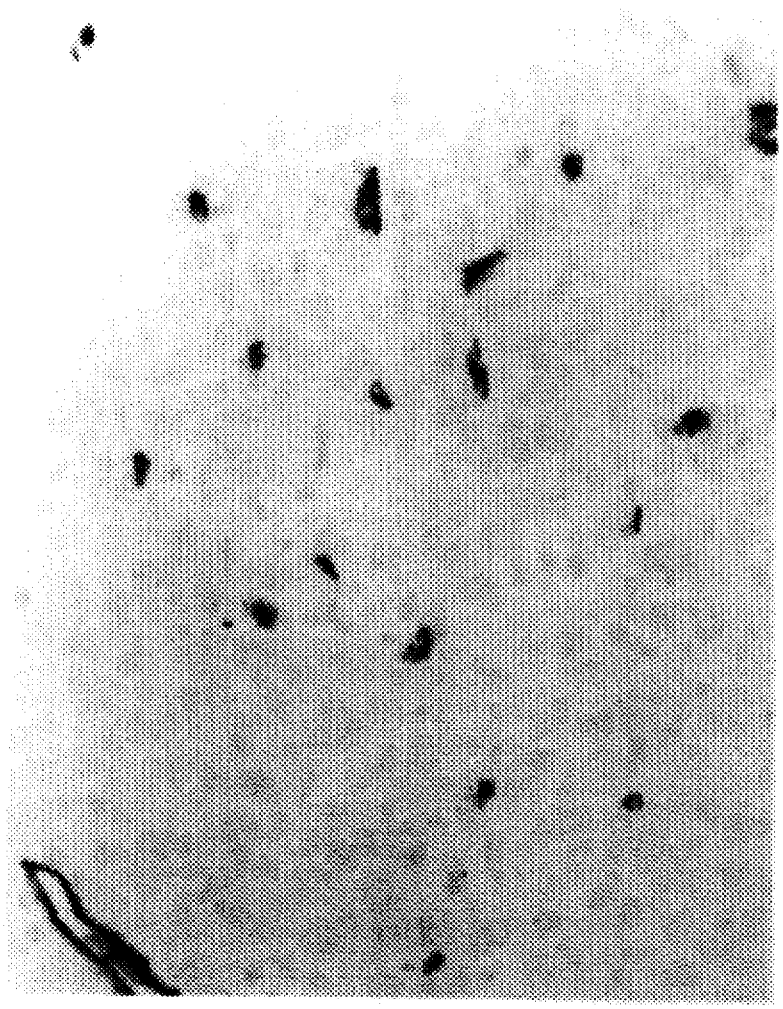
FIG. 5 is a photograph of an area of high grade carcinoma stained with an antibody to Factor VIII, showing a high density of small capillaries. There is variability of capillary morphology with several immunoreactive endothelial cells having tiny or inconspicuous lumens (340×).

As noted above, the present invention provides methods for estimating the biologic potential of prostate carcinoma in a patient, comprising the steps of (a) obtaining a tissue sample of prostate carcinoma from a patient, and (b) quantifying the vascularity of the tissue sample, and therefrom estimating the biologic potential of the prostate carcinoma. Within the context of the present invention, "biologic potential" should be understood to indicate the ability of a neoplasm to invade surrounding structures or spread to distant sites. For example, biologic potential refers to the ability of neoplasms, such as prostatic carcinoma, to metastasize, or the ability of gliomas to invade surrounding tissue.

Prior to obtaining a tissue sample from a patient for analysis, it is first generally preferable to examine the patient for the presence of a prostatic carcinoma. Typically, a patient is initially assessed for the possibility of prostate cancer by analysis of his serum for elevated levels of PSA (Prostate Specific Antigen, also termed "p30"). Tests kits which detect and analyze levels of PSA in serum may be obtained from a variety of sources (e.g., Hybritech Inc., San Diego, Calif.) (see also, U.S. Pat. No. Re., 33,405). Presence of prostatic cancer may then be confirmed by, for example, digital palpation of the prostate, and subsequently by needle biopsy, and histopathological analysis of the biopsy for cancer (discussed in more detail below).

In order to estimate the biologic potential of the prostatic carcinoma, a tissue sample must be obtained from the patient. Tissue samples of prostatic carcinoma may be obtained by a variety of methods, including for example, needle biopsy, trans-urethral biopsy, trans-urethral resection (TURP), simple open prostatectomy, or by total excision of the prostate.

Briefly, if the tissue samples are to be obtained by needle biopsy, samples are usually taken with a spring loaded gun (containing an 18 or 20 gauge needle) through either the skin or rectum under digital or ultrasound guidance.

If the tissue sample is to be obtained by trans-urethral biopsy, a cystoscope may be utilized to visualize the prostatic urethra, and a portion of the prostate removed using biopsy forceps. Alternatively, a resectoscope may also be utilized to remove a portion of the prostate. If the tissue sample is to be obtained by trans-urethral resection (TURP), the entire central portion or transitional-zone of the prostate is removed utilizing a resectoscope. The resultant prostate "chips" (which are approximately 0.5 to 3 $cm^3$ in size) may then be further sectioned (as discussed in more detail below).

Tissue samples may also be obtained either by simple open prostatectomy, or by the partial or entire surgical excision of the prostate. Briefly, for simple open prostatectomy, an incision is made in the abdomen, and the transitional zone of the prostate is removed through the prostatic capsule. Similarly, in order to remove the entire prostate, an incision is made in the abdomen and the entire prostate and surrounding tissue is excised.

Tissue samples that are obtained from the patient may then be analyzed for the presence of prostatic carcinoma using well-established techniques (see generally, "Theory and Practice of Histotechnology" Heehan and Hrapchak (eds.), C. V. Mosby Co., 1980, which is hereby incorporated by reference). Briefly, the samples are first "fixed" such that the sample maintains structural and physico-chemical integrity during subsequent processing. Various well-known methods may be utilized to fix the tissue samples, including for example, various alcohols, formaldehyde, and glutaldehyde.

Next, the samples are sectioned into thin (e.g., 1 to 10μ sections, and preferably, about 5μ sections) specimens which may be visualized by microscopy. The samples may be sectioned in a variety of ways, including for example, by first embedding the sample into a solid matrix such as paraffin or plastic, followed by sectioning of the sample.

Within an alternative embodiment, the tissue sample is fixed according to standard cryofixation techniques (see generally, "Theory and Practice of Histotechnology" Heehan and Hrapchak (eds.), C. V. Mosby Co., 1980). After the sample is frozen, it may be sectioned with a cryostat. This method is preferable when immunohistochemical techniques are employed which require that native proteins not be denatured by chemical fixation techniques.

The tissue samples may then be mounted on transparent (e.g., glass or Plexiglass) slides suitable for use with a conventional or inverted light microscope. Mounting may be performed simply by floating tissue samples in water or other fluid directly onto untreated slides. Alternatively, tissue samples may be placed onto slides by hand using a variety of small manipulating instruments (e.g., loops or applicators). Depending on the chosen processing procedure, it may also be useful to mount tissue samples on "coated" slides, which provide better adhesion of the sections or specimens under certain chemical treatments. Examples of suitable slide coating agents include lectins, albumins, and poly-amino acids such as poly-L-lysine.

Tissue samples may then be stained for histopathological examination. Typically, the tissue sample is first "cleared" of the embedding medium with an appropriate solvent, such as xylene or Histoclear (cryofixed tissues are not embedded prior to sectioning). The tissue sample is then processed for general histopathology, and subjected to a range of processing treatments, typically involving dehydration, rehydration and single or multiple staining and destaining procedures. A particularly preferred method for staining prostatic tissue samples involves the use of hematoxylin and eosin (H and E) (see generally, "Theory and Practice of Histotechnology" Heehan and Hrapchak (eds.), C. V. Mosby Col., 1980).

Other methods may also be utilized to enhance visualization of the carcinoma's vasculature, including for example, histochemical and immunohistochemical staining. Briefly, histochemical and immunohistochemical staining involve the use of specific tissue labeling procedures which enable even more precise identification of tissue components. In general, blood vessels contain many unique proteins and carbohydrate moieties. Ligands which react against these moieties may be utilized to stain the blood vessels. Representative examples of such ligands include lectins such as UEA-1 (*Ulex eropaeus*-1), and antibodies which react against blood vessel components. Within a particularly preferred embodiment, antibody against Factor VIII (DAKO, Cartinteria, Calif.) is utilized to mark the vessel surface. Such antibodies may be either labelled themselves, or reacted with a secondary antibody or label, such that the vessel surface may be visualized. A wide variety of labels may be utilized in this context, including for example, horseradish peroxidase, fluorescein-isothiocyanate, and rhodamine.

Within a preferred embodiment, sectional tissue samples are deparaffinized and rehydrated through graded alcohols. After blocking with normal horse serum, anti-Factor VIII antibody is applied and the sections are incubated overnight at 5° C. Secondary antibody (biotinylated goat anti-rabbit) is applied, followed by peroxidase avidin-biotin complex (ABC, Vector Labs, Inc.). Color is developed using diaminobenzidine (DAB) and slides are coverslipped for permanence.

The tissue sample may then be visualized in order to confirm that a tissue sample of prostatic cancer has been obtained. Such examination techniques are well known in the art (see generally, "Prostate Biopsy Interpretation", Epstein (ed.), Raven Press, 1989). The most common grading system for prostatic carcinomas is based on the Gleason system (see, Gleason et al., *J. Urol.* 111:58–64, 1974; Gleason et al., "Urologic pathology: The prostate", Tannenbaum ed., Lea and Febiger, Philadelphia, 1977; Mellinger et al., *J. Utol.* 97:331–337, 1967). Briefly, this system grades the glandular pattern of the tumor at relatively low magnification. Based upon primary (predominant) and secondary (second most prevalent) architectural patterns, the tumor is assigned a grade from 1 to 5.

Once a tissue sample of prostate carcinoma has been obtained, the vascularity of the sample is quantified in order to estimate the biologic potential of the carcinoma.

A variety of methods may be utilized to quantitate vascularity, including both indirect methods which measure factors associated with vascular components or blood vessel growth, and direct methods which directly quantitate blood vessels through manual or computer-aided morphometry. Indirect methods for determining vascularity may utilize ascitic fluids, or extracts of tissue samples obtained by a variety of methods, including for example, aspiration needle biopsy, needle biopsy, trans-urethral biospy or resection, simple open prostatectomy, or total excision of the prostate. A wide variety of factors may be quantitated in such samples, including for example proteins, carbohydrates, or other factors which are associated with vascular components or blood vessel growth. Representative examples include fibrin or fibrinogen (see, Svanberg, *Cancer*, 35:1382, 1975), as well as many "angiogenic factors" which are associated with blood vessel growth (e.g., angiogenic heparin-binding endothelial cell growth factors, angiogenin, transforming growth factors, and other angiogenic factors)(see Folkman et. al. *Science*, 235:442–447, 1987).

For either manual or computer aided morphometric quantitation, it is first desirable to prepare and stain the tissue sample as discussed above. Within one embodiment, the tissue samples may then be manually counted by placing the slide under a light microscope, and counting the number of blood vessels.

The histologic pattern of the microcirculation in benign prostatic tissue is generally similar in all cases. Briefly, the bulk of the smooth muscle stroma contains few venules and arterioles, with very few capillaries. In contrast, the stroma immediately adjacent to the epithelial basement membranes contains a rich network of capillaries investing each of the benign glands and ducts. The interval between adjacent capillaries at the gland-stroma interface is very regular in any given gland, but varies somewhat between glandular acini of differing morphology. Cystically dilated, atrophic glands lined by flattened or cuboidal epithelial cells have fewer, more widely spaced capillaries than hyperplastic glands with robust, columnar secretory epithelium. Glands of prostatic intraepithelial neoplasia (PIN) with crowded, piled-up epithelium and varying degrees of cytologic atypia are also associated with a capillary network in the adjacent stroma, similar to that seen in hyperplasia. Although the density in stromal tissue away from glands is generally low, focal areas with higher vascular density may be seen in some hyperplastic stromal nodules.

The appearance of microcirculation differs in carcinomas. Although carcinomas vary a great deal in their patterns of growth, the exquisite localization of capillaries at the interface of glands and stroma which characterizes benign tissues is not present in carcinoma. In carcinomas there is a generalized increase in the number of capillaries and no apparent orientation with respect to malignant glands and cells. In fields of very tightly packed malignant glands, the scanty stromal septa contain capillaries immediately adjacent to the malignant glandular profiles, but they do not surround the acini in a regular pattern as seen in benign tissue. No capillaries are present within the complex islands of epithelium in cribriform carcinoma, but there is a distinct periglandular capillary network. Thus, the major difference in architecture of the microcirculation in carcinoma appears to be an increased number of capillaries with a fairly uniform distribution, lacking the obviously asymmetric orientation around glandular acini which characterizes benign tissue.

The morphology of the individual vessels in carcinoma also differs from benign tissues. In benign tissues the capillaries are uniform in size and lumen caliber. In contrast, the capillaries in carcinoma are variable in size with several very small capillary buds having tiny or inconspicuous lumens.

As noted above, vascularity may also be quantitated utilizing computer-aided morphometry, utilizing a variety of digitizing devices (e.g., OPTIMAS, American Innovision, and NEXT). Within a preferred embodiment, slides are placed under a laboratory microscope for viewing by a video camera. The video image is then captured by a frame grabbing digitizing board in the computer that allows the live image to be frozen as a single frame for digital analysis.

An image analysis software package (OPTIMAS, Bioscan Inc., Edmonds, Wash.) is particularly preferred to manipulate and gather data from the frozen image. Briefly, the OPTIMAS image analysis package is designed to allow the user to write custom 'macros' for analyzing images. The macros are themselves computer programs that utilize 'objects' and 'functions' that have been provided in the OPTIMAS package. Functions and objects are computer programs written for expressed tasks, such as opening a file or running a mathematical manipulation on a digitized image. These 'canned' programs allow the user to choose from a large array of tasks without having to write the computer code. These functions and objects are essentially tools that can be used when constructing macro programs for specific tasks, such as counting vessels on tissue sections, or detecting cracks in a manufactured item. When writing a macro, the functions and objects desired for the task are combined with standard 'C' language programming code to construct a program that calls the functions and objects as they are needed.

A representative vessel counting macro (as set forth more fully in Appendix A and B) begins by allowing the user to open an existing data file, or open a new file. The desired image is then acquired, frozen as a digitized frame, and adjusted for contrast and brightness. As the macro runs, the user adjusts the foreground threshold to define the vessels. Retouching is done as required so as to accurately show the number of vessels, and a filter is run to further assure the accuracy of the count. Finally, the vessels are automatically counted and the number put into a data file, along with the area of the tissue analyzed. Within a preferred embodiment, the final vessel density value is expressed in vessels per $5 \times 10^{-3}$ mm$^3$ of tissue. Statistical analysis may then be performed using a spreadsheet program (e.g., Excel) as well as a more powerful statistical analysis program (e.g., Systat, Systat, Inc.)

Once vascular density has been determined, it may be utilized to estimate the biologic potential of the carcinoma. In general, a higher number of vessels for a given area is an indication of greater biologic potential. As an illustration, for a sectional area of $5 \times 10^{-3}$ mm$^3$, less than 100 vessels indicates a relatively low, biologic potential, 100 to 200 vessels an intermediate level of biologic potential, and greater than 300 vessels indicates a high level of biologic potential. It should be noted however, that measurement standards other than vessel number per area, may also be developed. For example, only vessels of a particular size or lumenal caliber may be counted. In like manner, only vessels which lack apparent orientation, or which differ from the standard circular or oval shape may be counted. A comparison of such aberrant vessels may similarly be utilized to estimate the biologic potential of a carcinoma (e.g., the higher "aberrant" vessel count, the greater the biologic potential).

As noted above, within a related aspect of the present invention, a method is provided for estimating the biologic potential of a selected carcinoma. Representative examples of selected carcinomas include: head and neck tumors, CNS tumors, melanomas and other skin tumors, lymphomas, soft tissue sarcomas, breast carcinomas, bladder carcinomas, pancreatic carcinomas, colon carcinomas, urothelial carcinomas, testicular carcinomas, cervical carcinomas, uterine carcinomas, renal carcinomas, ovarian carcinomas, hepatic carcinomas, pulmonary carcinomas, esophageal carcinomas, and gastric carcinomas.

Briefly, within this aspect of the present invention, a biopsy specimen is obtained from a selected carcinoma utilizing a procedure selected from the group consisting of needle biopsy, endoscopy, laproscopy, and cystoscopy. The specimen is then prepared as noted above. The vascularity of the tissue sample is then quantified utilizing the procedures set forth above, such that the biologic potential of the selected carcinoma may be estimated.

The following examples are offered by way of illustration and not by way of limitation.

EXAMPLES

EXAMPLE 1 PATIENT MATERIAL

Tissue from 15 patients, between 56 and 73 years of age, who had undergone radical prostatectomy at the Seattle Veterans Affairs Medical Center between March 1989 and April 1990 were examined. Cases were chosen to represent a spectrum of histologic patterns of varying Gleason grades, but within each individual case there was a region of relatively uniform Gleason pattern which was evaluated. Hematoxylin and eosin stained sections were examined by two histopathologists and Gleason grades were assigned. Five fields of carcinoma and five fields of benign prostatic tissue were stained with Factor VIII antibody, and quantified using a 4× objective and a 10× eyepiece.

Although most of the cancers contained a spectrum of histologic appearances with varying Gleason grades, we specifically chose areas for study where there were at least 5 low power microscopic fields (50×) of carcinoma with fairly homogeneous Gleason pattern. With this constraint, most of the tumors tended to be large. In particular, seven were stage B (confined within the prostate gland), seven stage C (local extension into the periprostatic soft tissue), and one was stage D with a single microscopic focus of lymph node metastasis. Clinical data on each of the cases is summarized in Table 1.

TABLE I

| AGE | GLEASON SCORE | PATHOLOGIC STAGE |
|---|---|---|
| 64 | 3 + 4 | B |
| 65 | 3 + 4 | B |
| 66 | 4 + 2 | B |
| 67 | 3 + 4 | B |
| 69 | 3 + 3 | B |
| 69 | 4 + 4 | B |
| 71 | 2 + 3 | B |
| 61 | 3 + 5 | $C_1$ |
| 65 | 3 + 4 | $C_1$ |
| 66 | 3 + 4 | $C_1$ |
| 73 | 3 + 4 | $C_1$ |
| 56 | 3 + 4 | $C_2$ |
| 71 | 3 + 4 | $C_2$ |
| 61 | 4 + 5 | $C_3$ |
| 73 | 3 + 4 | $D_1$ |

EXAMPLE 2 IMMUNOHISTOCHEMISTRY

Immunohistochemistry was performed using an ABC technique. Briefly, tissue from each case was processed routinely, fixed in 10% neutral buffered formalin, and embedded in paraffin. The archived blocks were sliced into 5 micron sections and mounted on poly-L-lysine coated slides. Sections were deparaffinized in Histoclear (National Diagnostics, Somerville, N.J.), rehydrated through graded ethanols, quenched in 0.3% $H_2O_2$ for 30 minutes, and covered with 5% normal goat serum for 30 minutes. After digestion in pronase (Sigma, St. Louis, Mo.) for 12 minutes, polyclonal rabbit antibody to human von Willebrand Factor, (Factor VIII) (Dako, Santa Barbara, Calif.) was applied to the sections at a dilution of 1:600 for 90 minutes at room temperature. After washing, the sections were incubated with biotinylated goat antibodies to rabbit immunoglobulins (Vector Laboratories, Burlingame, Calif.) for 30 minutes at room temperature. Following washing, an avidin-biotin-peroxidase complex (ABC Elite, Vector Laboratories) was applied to the sections according to the manufacturer's specifications. The slides were developed using diaminobenzidine (Polysciences, Warrington, Pa.) with 0.01% nickel chloride, to produce a black reaction product, and lightly counterstained with methyl green.

EXAMPLE 3 QUANTITATIVE MORPHOMETRY

Vessel counting was accomplished using a compound microscope (Nikon, Garden City, N.Y.) coupled to a black and white video camera with external image controller (Dage-MT1 CCD72, Michigan City, Ind.) via a video tube (Optec, Inc., Lowell, Mass.) to obtain a parfocal image for computer analysis. The image was digitized using a frame-grabbing board (Matrox Electronic System, Ltd., Dorval, Quebec) and a model 386 VGA computer (AGI ComputerInc., Fremont, Calif.) equipped with a mouse (Microsoft, Redmond, Wash.). The image was visualized on a high resolution RGB display monitor. The OPTIMAS image-analysis software package (Bioscan, Edmonds, Wash.) was employed for interactive manipulation of the image and data collection. Macros were employed as set forth in Appendix A. Statistical analysis was performed using Systat statistical software (Evanston, Ill.).

The method of computer aided morphometric quantitation is based on the ability to discriminate between the immunoreactive vessels, stained black, and the pale counterstain. A threshold level separating foreground from background was determined by the operator by visual inspection of the digitized image. The system was interactive allowing the operator to modify the image by comparison with the field under the microscope, thereby "erasing" non-specific black spots caused by endogenous peroxidase or other artifacts on the slide. Also, the contrast in areas of modest immunoreactivity could be enhanced to match the operator's assessment of the microscopic field. A threshold level of optimal distinction between positive immunoreactivity and background counterstain was set by the operator, and the gray scale image was converted to a binary black and white image. To this binary image a "filter" was applied which formed a 3 by 3 pixel grayscale averaging convolution, slightly blurring the image so that single vessels which occasionally appeared as a series of discrete points would blend into a single counted object. This filter did not combine any vessels which were considered separate by the investigators. The foreground objects (vessels) were then counted automatically.

In each of the 15 cases of radical prostatectomy, five fields of carcinoma were compared to five fields of benign prostate tissue. The fields of carcinoma were chosen on the basis of a uniform Gleason pattern of histology. Within this pattern the fields for examination were random, and there was no attempt to measure foci with particularly high or low vessel counts. After excluding bladder neck tissue and anterior fibromuscular stroma, the fields of benign tissue were also selected randomly comprising every other field in a single direction across the slide.

In order to test the validity of the computer aided morphometric quantitation technique, manual counts obtained by eye were compared with the counts obtained by the computer system on identical sections of prostate tissue reacted with antibodies to Factor VIII. Twenty fields were compared. The sections were examined at 100× magnification on a dual-headed microscope. A consensus was reached by both observers for each counted vessel. Following this determination, the same area was analyzed using the OPTIMAS software. The image analyzer was significantly faster than counting by eye and was very reproducible. The results comparing the two methods are presented in Table 2. At the [a]=0.05 level there was no significant difference between the two data sets. There is a slight positive bias in the image analysis method with a mean percent error of +2.8%. The standard deviation of the percent error is 7.9.

TABLE 2

| HISTOLOGY | MANUAL COUNT | COMPUTER COUNT | DIFFERENCE (%) |
|---|---|---|---|
| CANCER | 204 | 213 | 9 (4.4%) |
| BENIGN | 37 | 32 | −5 (−13.5%) |
| CANCER | 226 | 225 | 1 (−0.4%) |
| CANCER | 205 | 205 | 0 |
| CANCER | 195 | 195 | 0 |
| BENIGN | 87 | 82 | −5 (−5.8%) |
| CANCER | 81 | 72 | −9 (−11.1%) |
| CANCER | 87 | 93 | 6 (6.9%) |
| CANCER | 175 | 209 | 34 (19.4%) |
| BENIGN | 84 | 78 | −6 (−7.1%) |
| BENIGN | 42 | 46 | 4 (9.5%) |
| BENIGN | 85 | 85 | 0 |
| CANCER | 143 | 142 | −1 (−0.7%) |
| CANCER | 104 | 104 | 0 |
| BENIGN | 118 | 125 | 7 (5.9%) |
| CANCER | 198 | 200 | 2 (1.0%) |
| BENIGN | 180 | 206 | 26 (14.4%) |
| CANCER | 172 | 185 | 13 (7.6%) |
| CANCER | 109 | 111 | 2 (1.8%) |
| CANCER | 200 | 203 | 3 (1.5%) |
| MEAN | 136.6 | 140.6 | 4.0 (2.8%) |

A. Vascularity of carcinoma versus benign prostrate tissue in radical prostatectomy specimens In 15 prostatectomy specimens the vascularity of carcinoma was compared to the vascularity of benign prostate tissue in each specimen, utilizing computer-aided morphometric quantitation (Table 3). The microvessel density was higher in the areas of carcinoma than in the benign areas in each of the cases, but in one case the difference was statistically insignificant. The mean number of microvessels per $5 \times 10^{-3}$ $mm^3$ in the benign tissues was 72 (SD=30.9), with a range of 34 to 109 per case. The carcinomas had an overall mean microvessel count of 136 per square millimeter (SD =49.1) with a range of 66 to 205 per case. The mean ratio of vessel counts in carcinoma compared to benign tissue was 2.02 (SD=0.65), and overall, the fields of carcinoma were significantly more vascular than benign tissue (p<0.001).

TABLE 3

| CASE VALUE | HISTOLOGY | PER $5 \times 10^{-3}$ $mm^3$ | VESSELS S.D. | CA/ BENIGN | RATIO P |
|---|---|---|---|---|---|
| 1 | CANCER (3) | 66 | 6.7 | | |
|   | BENIGN | 48 | 7.2 | 1.37 | P < .005 |
| 2 | CANCER (3) | 180 | 25.0 | | |
|   | BENIGN | 92 | 5.5 | 1.96 | P < .001 |

TABLE 3-continued

| CASE VALUE | HISTOLOGY | PER $5 \times 10^{-3}$ mm$^3$ | VESSELS S.D. | CA/ BENIGN | RATIO P |
|---|---|---|---|---|---|
| 3 | CANCER (3) | 163 | 45.8 | | |
| | BENIGN | 103 | 22.0 | 1.58 | P < .05 |
| 4 | CANCER (2) | 150 | 30.2 | | |
| | BENIGN | 109 | 19.6 | 1.38 | P < .05 |
| 5 | CANCER (3) | 103 | 16.4 | | |
| | BENIGN | 48 | 10.4 | 2.14 | P < .001 |
| 6 | CANCER (4) | 139 | 12.4 | | |
| | BENIGN | 78 | 25.6 | 1.76 | P < .001 |
| 7 | CANCER(3) | 112 | 18.7 | | |
| | BENIGN | 34 | 13.4 | 3.28 | P < .001 |
| 8 | CANCER (3) | 110 | 13.5 | | |
| | BENIGN | 78 | 36.4 | 1.41 | NS |
| 9 | CANCER (3) | 124 | 42.6 | | |
| | BENIGN | 38 | 9.0 | 3.14 | P < .005 |
| 10 | CANCER (3) | 175 | 48.6 | | |
| | BENIGN | 94 | 22.2 | 1.86 | P < .01 |
| 11 | CANCER (2) | 130 | 26.0 | | |
| | BENIGN | 82 | 30.2 | 1.60 | P < .005 |
| 12 | CANCER (2) | 205 | 40.1 | | |
| | BENIGN | 97 | 23.7 | 2.12 | P < .001 |
| 13 | CANCER (3) | 86 | 14.6 | | |
| | BENIGN | 66 | 7.1 | 1.32 | P < .05 |
| 14 | CANCER (3) | 204 | 27.8 | | |
| | BENIGN | 76 | 29.7 | 2.68 | P < .001 |
| 15 | CANCER (4) | 90 | 9.3 | | |
| | BENIGN | 36 | 5.9 | 2.53 | P < .001 |
| MEAN | CANCER | 135.9 | 49.1 | | |
| | BENIGN | 71.9 | 30.9 | 1.95 | P < .001 |

B. Vascularity of organ confined versus metastatic prostate carcinomas

Vascularity, as determined by computer aided morphometric quantitation, was compared between 13 specimens of prostatic carcinoma which had metastasized to the lymph nodes or bone and/or other parts of the body (Table 4), and 14 prostatic carcinoma specimens which had remained organ confined (Table 5). These specimens were obtained by radical prostatectomy (RP), or transurethral resection of the prostate (T). In the organ confined cases, the carcinoma was entirely confined to the prostate, as determined by conventional histopathological examination methods. In the metastatic cases, the carcinoma had metastasized either to the patient's lymph nodes (D1), or to the bone and/or other parts of the patient's body (D2). Histologic grade of the specimens was also determined, using the Gleason grading system. The overall microvessel density in the metastatic cases was higher than in the organ confined cases. The mean number of microvessels per $5 \times 10^{-3}$ mm$^3$ in the metastatic cases was 134 microvessels per square millimeter, with a range of 55 to 306 per case. The mean microvessel density for cases with organ confined carcinoma was 106, with a range of 55 to 150.

TABLE 4

| | STAGE D CASES | | | |
|---|---|---|---|---|
| # | STAGE | RP/T | MEAN | ST DEV |
| 1 | D1 | RP | 124.08 | 42.60 |
| 2 | D1 | RP | 55.07 | 17.86 |
| 3 | D1 | RP | 196.38 | 45.90 |
| 4 | D1 | RP | 62.03 | 10.46 |
| 5 | D2 | T | 159.13 | 25.47 |
| 6 | D2 | T | 162.75 | 24.97 |
| 7 | D2 | T | 306.52 | 110.07 |
| 8 | D2 | T | 58.26 | 25.02 |

TABLE 4-continued

| | STAGE D CASES | | | |
|---|---|---|---|---|
| # | STAGE | RP/T | MEAN | ST DEV |
| 9 | D2 | T | 199.57 | 40.05 |
| 10 | D2 | T | 95.94 | 29.77 |
| 11 | D2 | T | 88.26 | 39.05 |
| 12 | D2 | T | 155.65 | 44.24 |
| 13 | D2 | T | 100.58 | 63.41 |
| 14 | D2 | T | 113.62 | 32.48 |

TABLE 5

| | ORGAN CONFINED CASES | | | |
|---|---|---|---|---|
| # | GRADE | RP/T | MEAN | ST DEV |
| 1 | 2 | RP | 150.37 | 30.19 |
| 2 | 2 | RP | 78.26 | 18.51 |
| 3 | 2 | RP | 130.43 | 26.01 |
| 4 | 2 | RP | 91.45 | 6.45 |
| 5 | 3 | RP | 144.64 | 21.07 |
| 6 | 3 | RP | 85.07 | 8.72 |
| 7 | 3 | RP | 66.09 | 6.67 |
| 8 | 4 | RP | 85.80 | 14.64 |
| 9 | 2 to 3 | RP | 109.71 | 30.16 |
| 10 | 2 to 3 | RP | 148.70 | 29.06 |
| 11 | 2 to 4 | RP | 104.20 | 27.21 |
| 12 | 2 to 4 | RP | 129.96 | 35.25 |
| 13 | 4 to 5 | RP | 58.12 | 33.71 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

APPENDIX A

```
/* This Macro is designed to count blood vessels
   stained with anti-Factor VIII antibody.
PositionWindow ("Macro", 473, 153, 168, 198);
DataCollection (-1);
PositionWindow ("OPTIMAS", 10, 13, 367, 100);
PositionWindow ("Data", 391, 13, 98, 118);
SetExport (ArArea,1,TRUE);
Prompt("Select a Data File");
    /* Ask the user to choose the data file */
DataFile();
Lo = IntConfigData[34];
        /* Range of threshold is stored here */
Hi = IntConfigData[35];
while (Prompt ("Would you like to examine a sample?"))
    { /* Ask the user if they would like to select a new Region
         Of Interest
    */
            /* or use the pre-defined Region Of Interest already created.
    */
    If (Prompt ("would you like to reset contrast?"))
        { Acquire (FALSE);
          Contrast (FALSE);
          Freeze ();
          RunMacro(Path Variable:"GetImage.Mac"); }
    else{RunMacro(Path Variable:"GetImage.Mac"); }
        If (Prompt("Would you like to select a new Region Of
        Interest?"))
            { ClearScreen();
              SelectROI();
              CreateArea(); }
        else {
              ClearScreen();
```

APPENDIX A

```
        SelectROI (2.10329 : 19.9812 : 26.8169 : 1.00782);
        CreateArea (2.10329 : 19.9812 : 2.10329 : 1.00782 :
26.8169 : 1.00782: 26.8169 : 19.9812 : 2.10329 : 19.9812 : 2.10329 :
19.9812);}
ImageToBuffer ();
Extract ();
Export(ArArea);
                        /* In calibration units */
Retouching();
                        /* Open retouch box */
Threshold ();
                        /* First threshold */
GrayToBinary ();
                        /* Convert to black and white */
Convolve (0.0 : 20.989 ::
28.0 : 0.0, 3, 3, 1 : 1 : 1 : 1 : 1 : 1 : 1 : 1 : 1, 9);  /* 3x3 average filter */
InvertFilter();
Threshold ();
                        /* Second threshold */
CreateArea (, FALSE, TRUE);
MacroMessage ("Total Area = ", ArArea);
TallyExport ();
                        /* Count areas and export to data file */
}
/* This Macro is designed to measure the length of PIN
   gland outlines count associated blood vessels
   stained with anti-Factor VIII antibody.
        PositionWindow ("Macro", 473, 153, 168, 198);
        INTEGER VesselCount;
        SetExport(LnLength,0,TRUE);
        SetExport(VesselCount);
Prompt(" Select a Data File");
        /* Ask the user to choose the data file */
        DataFile();
If (Prompt ("Hit OK if using 4X lens, CANCEL if using 10X lens"))
        {    LoadFromOPTfile("fourx.cfg", "fourxcalib");
             Calibrate(fourxcalib);
        }
else
        {    LoadFromOPTfile("tenx.cfg", "tenxcalib");
             Calibrate(tenxcalib);
        }
If (Prompt ("Load Global Background Correction?"))
        RunMacro ("C:/OPTIMAS3/DIALOGS/correct.mac");
while (Prompt ("Would you like to examine a sample?"))
ain Loop*/
        {
        Acquire (FALSE);
        Contrast (255);
        Prompt("    Freeze");
        Freeze ();
        SelectFullScreen();
        MacroMessage (" Apply Background Correction if desired, \n\n
then click OK");
        while (Prompt ("Draw Line?"))
                                /*Draw Multiple Lines */
            {    CreateLine();
                 Extract();
                 Export(LnLength);
                 VesselCount = Prompt ("How many vessels associated
with this gland?", "INTEGER"); /* Enter number of vessels associated
with gland*/
                 Export(Vesselcount);
            }
            If (Prompt (" Set Threshold?"))
                 Threshold ();
        }
/* Use the following code to use the 40X lens:
(Prompt ("Are you using the 40X lens?"));
                 LoadFromOPTfile("fortyx.cfg", "fortyxcalib");
                 Calibrate(fortyxcalib);)
Trade the entire 4X/10X 'If' block with this code.
*/
```

I claim:

1. A method for estimating the biologic potential of a selected carcinoma in a patient, comprising:

obtaining a limited random biopsy sampling of a carcinoma; and quantifying the vascularity of said biopsy sampling, and therefrom estimating the biologic potential of the selected carcinoma.

2. A method according to claim 1 wherein said step of quantifying vascularity comprises computer-aided morphometric quantification of vascular components in the biopsy specimen.

3. A method according to claim 1 wherein the carcinoma is selected from a group consisting of head and neck tumors, CNS tumors, melanomas and other skin tumors, lymphomas, soft tissue sarcomas, prostate carcinomas, breast carcinomas, bladder carcinomas, pancreatic carcinomas, colon carcinomas, urothelial carcinomas, testicular carcinomas, cervical carcinomas, uterine carcinomas, renal carcinomas, ovarian carcinomas, hepatic carcinomas, pulmonary carcinomas, esophageal carcinomas, and gastric carcinomas.

* * * * *